(12) United States Patent
Carlson et al.

(10) Patent No.: US 6,650,108 B2
(45) Date of Patent: Nov. 18, 2003

(54) SYSTEM AND METHOD FOR MONITORING THE COMPOSITION OF A MAGNETORHEOLOGICAL FLUID

(75) Inventors: J. David Carlson, Cary, NC (US); Gary W. Adams, Holly Springs, NC (US)

(73) Assignee: Lord Corporation, Cary, NC (US)

( * ) Notice: Subject to any disclaimer, the term of this patent is extended or adjusted under 35 U.S.C. 154(b) by 98 days.

(21) Appl. No.: 09/854,071

(22) Filed: May 11, 2001

(65) Prior Publication Data

US 2003/0020463 A1 Jan. 30, 2003

(51) Int. Cl.[7] .............................................. G01N 27/74
(52) U.S. Cl. ................... 324/204; 73/861.354; 340/631
(58) Field of Search ................................. 324/204, 232, 324/233, 234, 236; 73/861.354, 861.11; 422/88; 340/573.4, 632, 631

(56) References Cited

U.S. PATENT DOCUMENTS 4,004,216 A * 1/1977 Natens et al. ................. 324/41
4,476,434 A * 10/1984 Collins et al. ............... 324/233
5,608,316 A * 3/1997 Cryton et al. ................ 324/204

FOREIGN PATENT DOCUMENTS

| EP | 0 157 496 A2 | 10/1985 |
| EP | 0 157 496 | 10/1985 |

OTHER PUBLICATIONS

"Density" Paul N. Gardner Co., Inc. General Catalog, 1997.

* cited by examiner

*Primary Examiner*—N. Le
*Assistant Examiner*—Subhash Zaveri
(74) *Attorney, Agent, or Firm*—Edward F. Murphy, III

(57) ABSTRACT

A system and method for monitoring the composition of a magnetically permeable material, where the system comprises a first container containing a volume of magnetically permeable material; a flow path for flowing the magnetically permeable material out of the container; a sensor for determining the inductance of the magnetically permeable material; and a sensor for determining the density of the magnetically permeable material. The sensors for determining the density and inductance of the magnetically permeable material are flow connected to the flow path.

26 Claims, 8 Drawing Sheets

SYSTEM AND METHOD FOR MONITORING THE COMPOSITION OF A MAGNETORHEOLOGICAL FLUID

FIELD OF THE INVENTION

The invention relates to a system and method for monitoring the composition of a magnetically permeable material which may be a magnetically permeable fluid. More particularly the invention relates to a system and method for monitoring the composition of a magnetically permeable material by sensing the inductance of the material and mass flow rate of the material through the system. The sensed values of inductance and mass flow rate may be used separately or in combination to determine the actual volume fraction of particles in the material.

BACKGROUND OF THE INVENTION

Magnetically permeable materials such as magnetorheological (MR) fluid is comprised of magnetizable particles suspended in a liquid, which might be oil, water or silicone for example. Before the introduction of a field, such MR fluids are typically free flowing. With the introduction of a field, such as a magnetic field, the particles form a dense network and the apparent viscosity of the fluid changes making the fluid thick. The degree of change is proportional to the magnitude of the applied magnetic field.

Magnetically permeable materials are frequently used to control the displacement of a moving member such as a piston in a damper or a rotating component in a braking device. Such materials are specifically designed to suit the associated application for the fluid. The specifically designed materials must have the requisite volume fraction of magnetizable particles and must include the requisite type of iron in order to be able to provide the requisite resistive forces that produce the requisite motion control of the associated device.

The magnetically permeable material, such as MR fluid, is manufactured by mixing the iron particles and carrier fluid. The iron particles and carrier fluid must be mixed at the precise ratios to produce a volume of fluid with the required magnetic properties. As the fluid is mixed, the fluid is tested by a technician to ensure that the required consistent fluid composition is achieved and maintained. The prior art method for testing the magnetically permeable material is comprised of using a density cup manufactured by Paul Gardner Group of Pompano Beach, Fla. to test discrete volumes of the material. In practice, a volume of collected in the density cup. Once the density cup is filled with the required volume of fluid, the precise collected volume of the viscous fluid is determined using a complex method that involves diluting and mixing the sample of the fluid with an acceptable diluting agent which frees the viscous material sample of entrapped air. The diluted sample is then weighed and from the weight and fluid volume the volume fraction of magnetizable particles may be determined.

There are a number of problems associated with the method for testing the manufactured magnetically permeable material using a density cup. First, the material is tested intermittently. Because the material is tested discretely rather than continuously, only a small portion of the total volume of material is sampled. As a result, the mixed material composition may be inconsistent and comprised of variable and undesirable volume fractions of magnetizable material. Additionally, the density cup sampling procedure is highly specialized and requires specific, extensive training in order to develop the expertise needed to regularly obtain accurate measurements. Therefore, the density cup testing technique is prone to operator error.

The foregoing illustrates limitations known to exist in present systems and methods. Thus, it is apparent that it would be advantageous to provide an alternative system and method for monitoring the fluid composition to maintain a desired volume fraction and type of magnetizable particles where the volume fraction of the material is measured continuously as the material is mixed and is not prone to operator error. Accordingly, a suitable alternative method and system is provided including features more fully disclosed hereinafter.

SUMMARY OF THE INVENTION

In one aspect of the present invention this is accomplished by a system and method for monitoring the composition of a magnetically permeable material, where the system comprises a first container containing a volume of magnetically permeable material; a flow path for flowing the magnetically permeable material out of the container; a sensor for determining the inductance of the magnetically permeable material; and a sensor for determining the density of the magnetically permeable material. The sensors for determining the density and inductance of the magnetically permeable material are flow connected to the flow path.

More specifically, the invention uses an inductance sensor that is sensitive to the magnetic permeability of a magnetorheological fluid to measure or monitor the volume fraction of magnetic particles in the magnetically permeable fluid. The sensing inductor is generally hollow with a coil surrounding the hollow body. The hollow member may be annular or tubular. An inductance meter or bridge circuit is used to measure the inductance of the coil. The measured inductance is proportional to the magnetic permeability of the material contained in the coil. In this way, the desired volume fraction in the material is maintained. The density of the material is monitored by a mass flow meter which may be a Coriolis type flow meter for example. By measuring the material density a technician can confirm that the required type of magnetic particles were mixed with the carrier fluid.

The values of inductance and mass flow rate may be used separately or in combination to determine the particle volume fraction.

The foregoing and other aspects will become apparent from the following detailed description of the invention when considered in conjunction with the accompanying drawing figures.

DETAILED DESCRIPTION OF THE PREFERRED EMBODIMENTS

Figure 1:
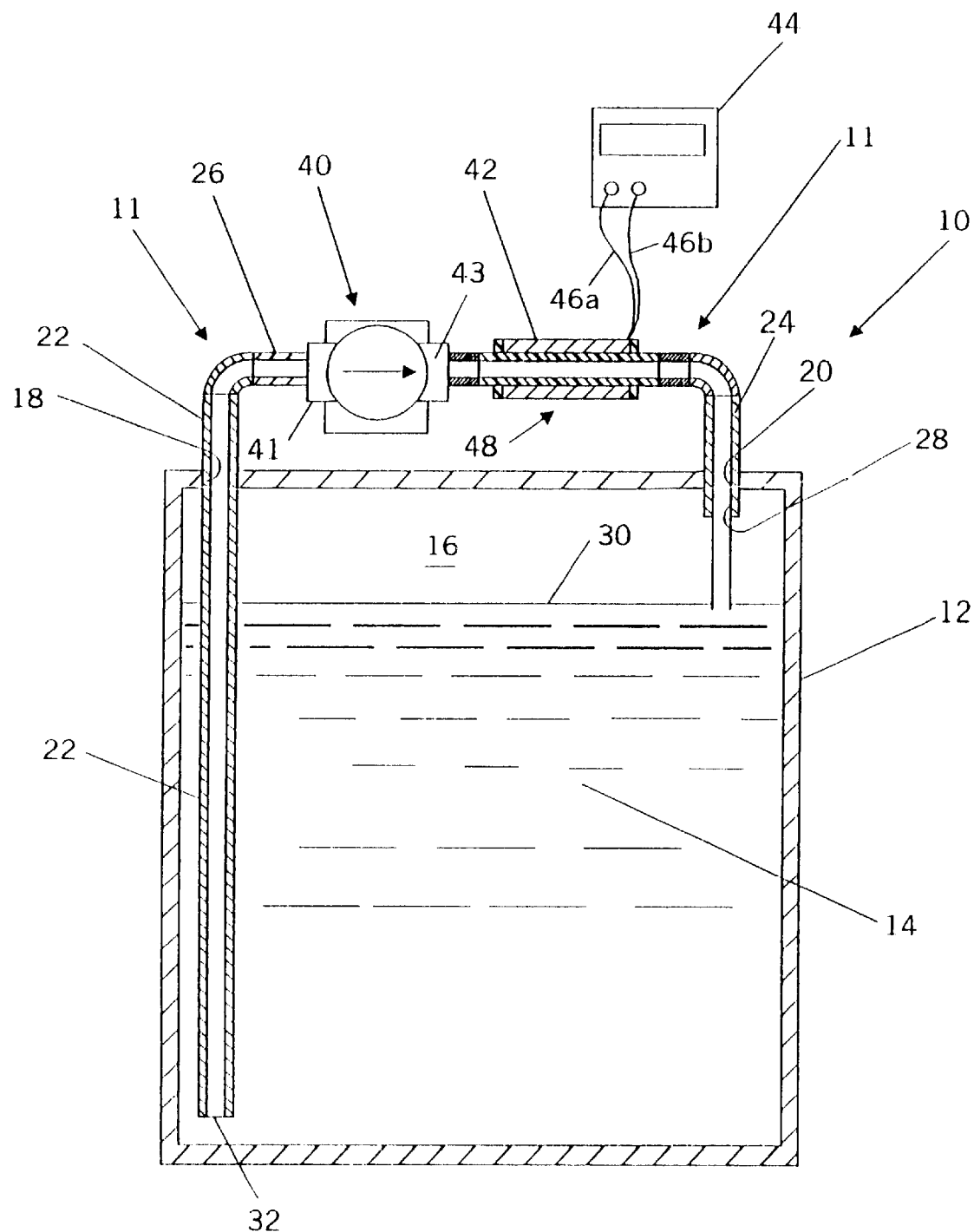
FIG. 1 is a schematic representation of a first embodiment of the present invention system for monitoring the composition of a magnetically permeable material.

Turning to the drawings wherein like parts are referred to by the same numbers in the views, a first embodiment system 10 for monitoring the composition of a magnetically permeable material such as a field responsive material including a magnetorheological (MR) fluid, is illustrated in FIGS. 1–6. It should be understood that the system and method of the present invention may be used to monitor the composition of a variety of magnetically permeable materials, including materials that are useful as coatings for computer related devices and storage mediums. However, as the description proceeds, for purposes of describing a preferred embodiment of the invention the exemplary magnetically permeable material monitored and analyzed by the present invention will be MR fluid. As shown in FIG. 1 the system 10 generally comprises substantially closed volume container 12 that houses a volume of magnetically permeable fluid 14 in container chamber 16.

Openings 18 and 20 are provided along the container and the openings provide means for locating portions of outlet and return conduits 22 and 24 in chamber 16. For purposes of describing the preferred embodiments of the invention the openings are provided in the top of the container. The outlet and return conduits are flow connected by an intermediate conduit section 26. The intermediate section 26 may be comprised of one or more conduit segments which may be comprised of any suitable combination of elbows, tee's and straight segments well known to one skilled in the relevant art. As shown in FIG. 1, the outlet 28 of return conduit is located above fluid level 30 and the inlet end 32 of outlet conduit 22 is located below the fluid level 30. The means for flowing the fluid out of the container 12 and returning the fluid to the container fluid chamber 16 may be comprised of a single unitary conduit member comprised of outlet, intermediate and return sections or may be comprised of a combination of discrete members such as outlet conduit 22, intermediate conduit 26 and return conduit 24. Hereinafter, the means for flowing the fluid out of the container and returning the fluid to the container shall be generally referred to as the "flow path" and this term shall be understood to mean a flow means comprised of either discrete members or a unitary member. The flow path may also be referred to by its discrete conduits or sections. As shown in FIG. 1, the first embodiment system of the present invention comprises a single container 12 and the fluid 14 is drawn out of the container flowed through flow path 11 and returned to the fluid volume 14.

Means for urging the material through the system such as conventional pump 40 is flow connected to intermediate conduit 26 along the length of the intermediate conduit segment. The pump 40 includes pump inlet 41 and pump discharge 43 and may be comprised of any suitable well known pump such as a diaphragm pump. The pump serves to draw the fluid out of the container and pump it through the intermediate segment and back into container 12.

A sensing inductor 48 is flow connected to intermediate conduit 26 downstream from pump discharge end 43. The inductor 48 in turn is electrically connected to output device 44 such as an inductance meter, so that the meter is in signal receiving relation with the inductor. The output device may be any suitable device that reliably displays the inductance sensed by sensing inductor 48. Connection members 46a and 46b electrically connect the device 44 to the sensing member 48 in a conventional manner. Although the sensing inductor 48 is shown and described as being upstream from the pump, it should be understood that alternatively, the pump could be located upstream from the sensing inductor 48.

The sensing inductor 48 includes a primary coil 42. The primary coil 42 may be comprised of 2300 turns of number twenty-five AWG magnet wire 50 wound around the outside of a length of a hollow tubular core member 52. The material comprising the core member 52 is a non-magnetic and non-electrically conductive material, such as polyvinylchloride known to those skilled in the art as PVC. It is critical that the core be made from a material that is both non-magnetic and non-conductive. If the core were conductive the core would act as a magnetic shield that would prevent the sensor 42 from effectively probing the Magnetically permeable material and thereby would reduce the sensitivity and accuracy of the sensing inductor 48.

Figure 2:
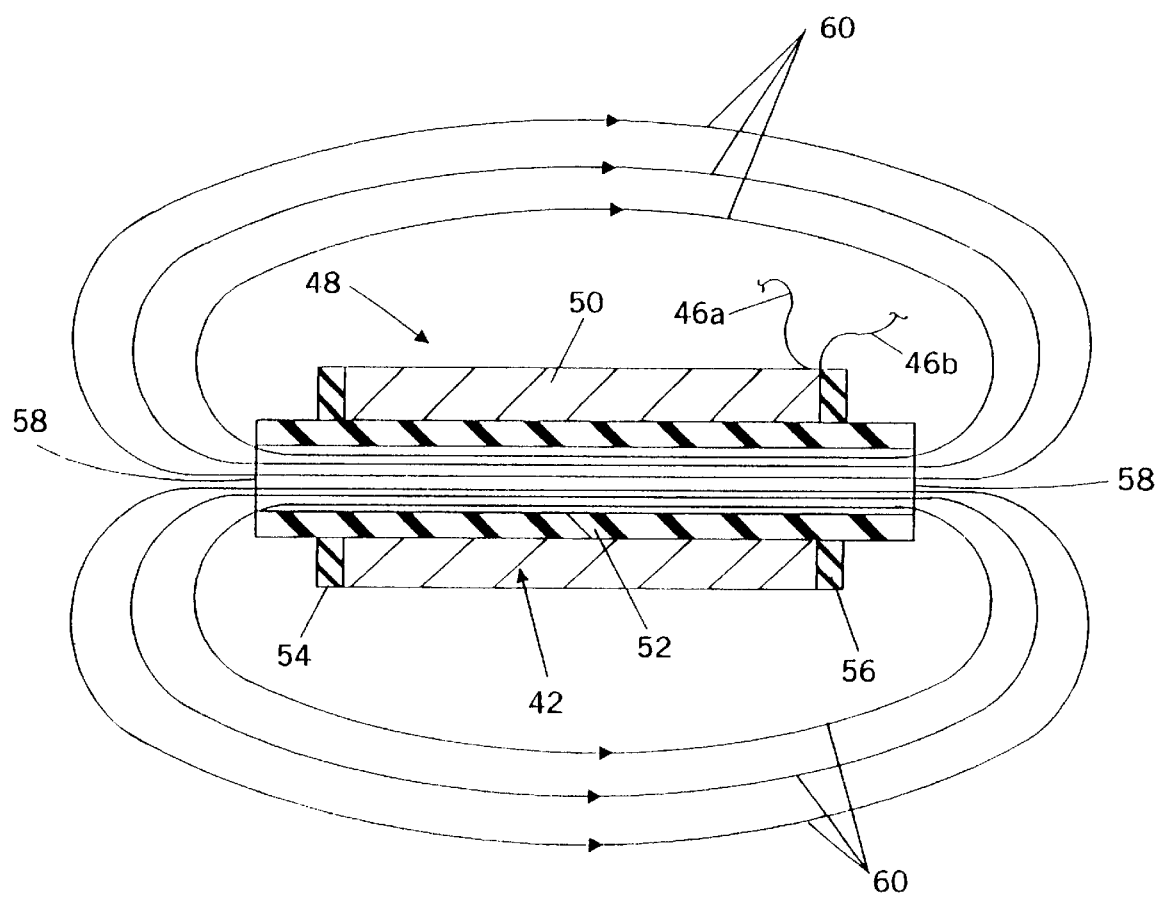
FIG. 2 is a schematic representation of the sensing inductor of the present invention including the magnetic field produced by the sensing inductor coil.
Figure 3A:
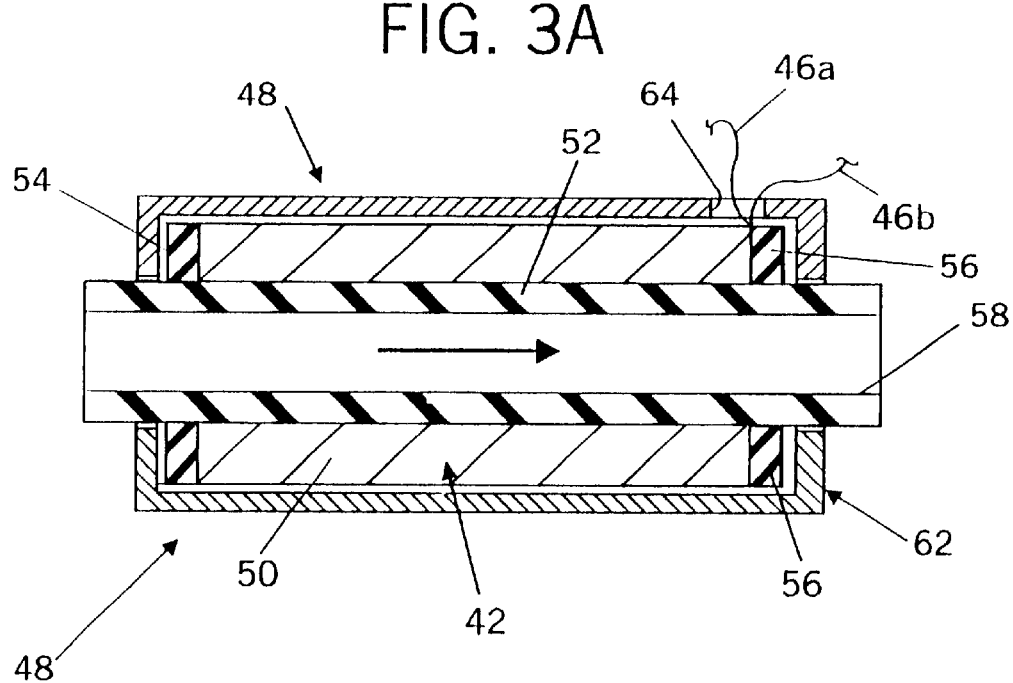
FIG. 3A is a schematic representation of the sensing inductor of FIG. 2 with a shield surrounding the sensing inductor.
Figure 3B:
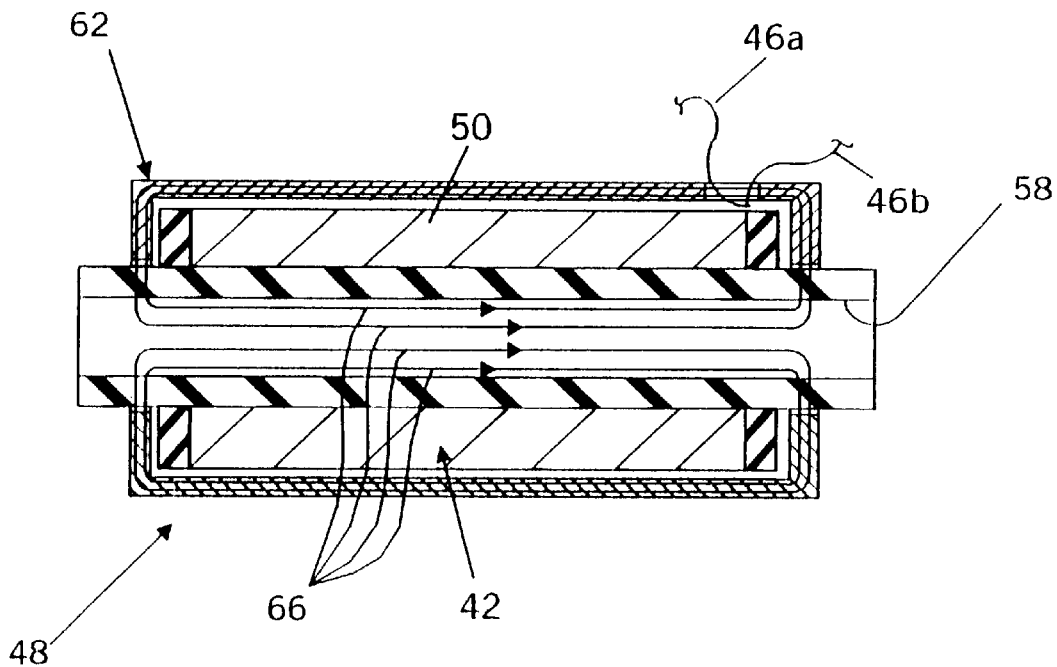
FIG. 3B is a schematic representation of the sensing inductor of FIG. 3A including the magnetic field produced by the sensing inductor coil.

As shown in FIG. 2, the magnet wire is wound around the tubular member 52 between annular flange members 54 and 56 located proximate the member ends. The annular flange members are comprised of rubber grommets and serve to contain the wire therebetween along a portion of the length of the member 52. As shown in FIGS. 3A and 3B, the member 52 defines core chamber 58.

The magnetic field lines shown in FIG. 2 illustrate the approximate shape of the magnetic field 60 that is established by the magnet wire comprising the primary coil 50. The field lines pass through the Magnetically permeable material located in the hollow core chamber 58 and around the core ends.

The display device 44 includes an operating frequency such as 1000 Hz. The device causes an excitation in the coil and in this way establishes magnetic field 60 that extends substantially axially through the coil 50 and through chamber 58. If the core were an electrical conductor such as copper for example, the core would act as a secondary coil in which circumferential electrical currents are induced. Such secondary currents would produce magnetic fields that would oppose and cancel the primary magnetic field 60 in the Magnetically permeable material. The conductive core would act as a magnetic shield and prevent the sensor 48 from probing the fluid and thereby reducing the sensitivity of the device 48.

It is expected that the system and method of the present invention will be able to detect volume fraction changes of less than one percentage point. During use, when the magnetic field is established by inductor coil 50, the field interacts with the fluid passing through chamber 58 of the inductor 48. The greater the volume fraction of iron particles in the fluid, the greater the magnetic reaction of the fluid. Thus the system 10 senses changes in the volume fraction of fluid 14.

A test of the system 10 of the present invention was conducted on or about Jan. 22, 2001. Initially during the fluid volume 14 had an iron volume fraction of 0.15 and the inductance sensed by device 42 and indicated by output device 44 was 28.8 mH. The fluid 14 was diluted by adding 250 ml of oil to the overall 3.0 liters of 15% volume fraction (v/v) fluid. By diluting the fluid in this manner, the volume fraction was lowered to 14% v/v. As the pump recirculated the Magnetically permeable material it acted as a mixer. As the fluid was mixed the device 44 displayed the changing fluid inductance sensed by sensor 48. The inductance started at 28.8 mH and over time the inductance value decreased to 27.1 mH. Thus, the 1% change in volume fraction corresponded to slightly more than a 2.5% change in the inductance reading. The inlet section of the flow path was moved to various locations in the container and the inductance reading was observed on the display device 44. The inductance reading was the same at the various locations in the container. In operation, the inductance meter provides a value representing the magnetic permeability of the material in the system. When the inductance meter is used singly to determine the material volume fraction, a particle density is assumed by the system operator or technician in order to infer a volume fraction for the material. In practice, the density may be assumed with great accuracy to thereby provide a precise volume fraction value.

The sensitivity of the sensing inductor 48 shown in FIGS. 1 and 2 may be increased in the manner shown in FIGS. 3A and 3B. As shown in FIGS. 3A and 3B, the sensing inductor 48 may be modified by adding an external shield 62 that substantially surrounds the member 52, flanges 54 and 56 and coil 42 of sensing inductor 48. The shield includes an opening for passing connection members 46a and 46b through the shield. The shield is made from any suitable material of high magnetic permeability such as a low carbon steel. The external shield prevents interference from external sources and also provides low reluctance flux return path 66. See FIG. 3B. As a result of the introduction of the shield 62, a greater portion of the magnetic field energy is contained in the fluid passing through the sensor 48 rather than being dispersed into the environment surrounding the system 10.

Figure 4:
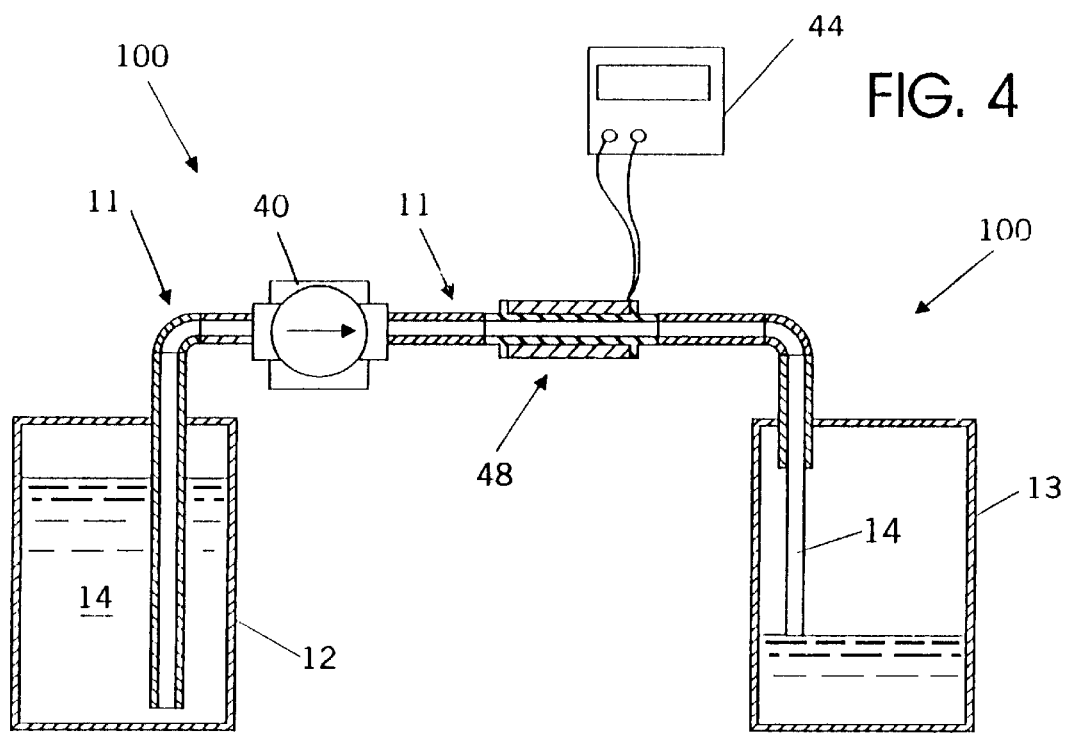
FIG. 4 is a schematic representation of a second embodiment of the present invention system for monitoring the composition of a magnetically permeable material.

A second embodiment system 100 is illustrated in FIG. 4. The second embodiment system 100 comprises container 12, pump 40, sensing inductor 48 output device 44 and flow path 11 as previously described in connection with system 10. The system 100 includes a second container 13 that is adapted to receive the fluid 14 that is discharged from the return section of flow path 11. Thus the fluid 14 is drawn from container 12, flowed through conduit 11 and is flowed into receptacle 13. If the fluid is of the required volume fraction, the fluid that is collected in receptacle 13 may be used for its intended application.

Figure 5:
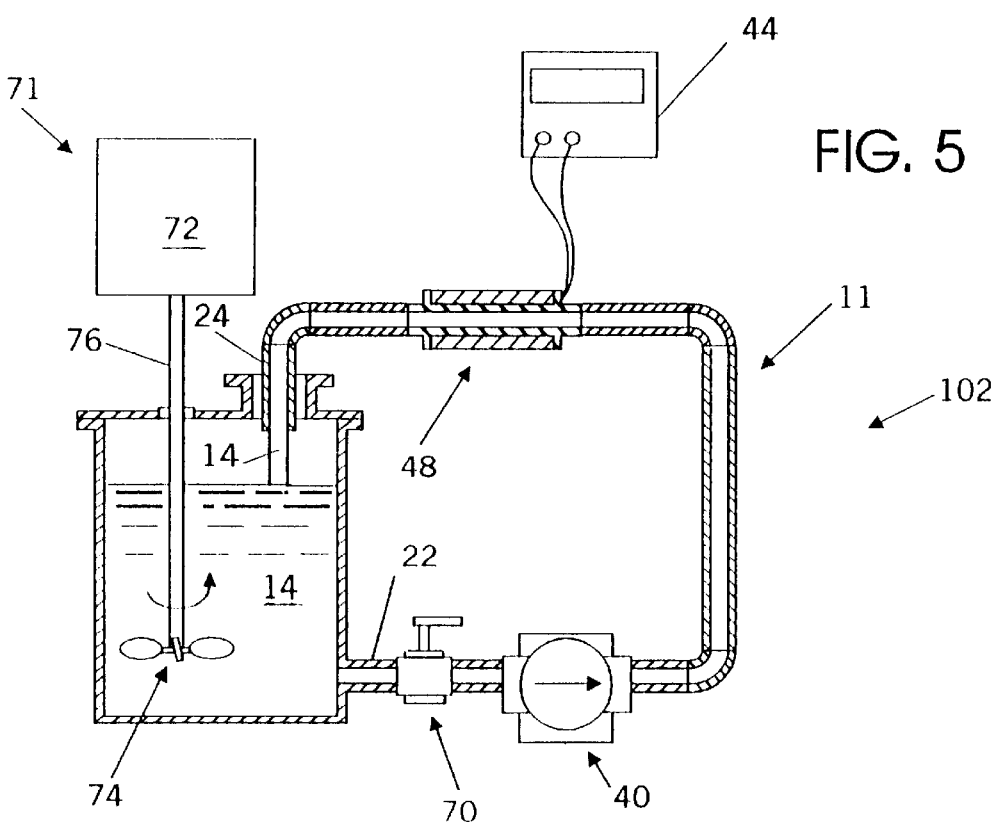
FIG. 5 is a schematic representation of a third embodiment of the present invention system for monitoring the composition of a magnetically permeable material.

A third embodiment system 102 is illustrated in FIG. 5. The system 102 includes sensing inductor 48, output device 44, pump 40, container 12 and flow path as previously described. In the flow path 11, the outlet conduit 22 is located proximate the bottom of the container 12 and the return conduit 24 is located at the top of the container. A conventional mixing device 71 serves to mix the fluid 14 in the container. The device 71 comprises a motor 72 that is fixed to an agitation member 74 by a rigid shaft 76. The motor may be an electric motor. The agitation member 74 is located proximate the bottom of the container but may be located in any suitable position in the container. A valve 70 is flow connected along flow path 11 upstream of the pump 40. The valve may be any suitable conventional valve such as a butterfly valve for example. In this way, the fluid is mixed as it is flowed through the system and is also mixed by agitation element 74 before it is drawn into the flow path.

Additionally, the system 102 could be modified to include a second container 13, so that the fluid is flowed into the second container in the manner previously shown and described in second embodiment system 100. In such a modified system 102, the inlet would be connected to the container 12 as shown in FIG. 5 and the discharge end would be relocated to a position away from the container 12 and adjacent container 13.

The system 102, serves to monitor the composition of the magnetically permeable fluid 14 in the manner previously described in conjunction with system 10, therefore further description of the operation of system 102 is not required.

Figure 6:
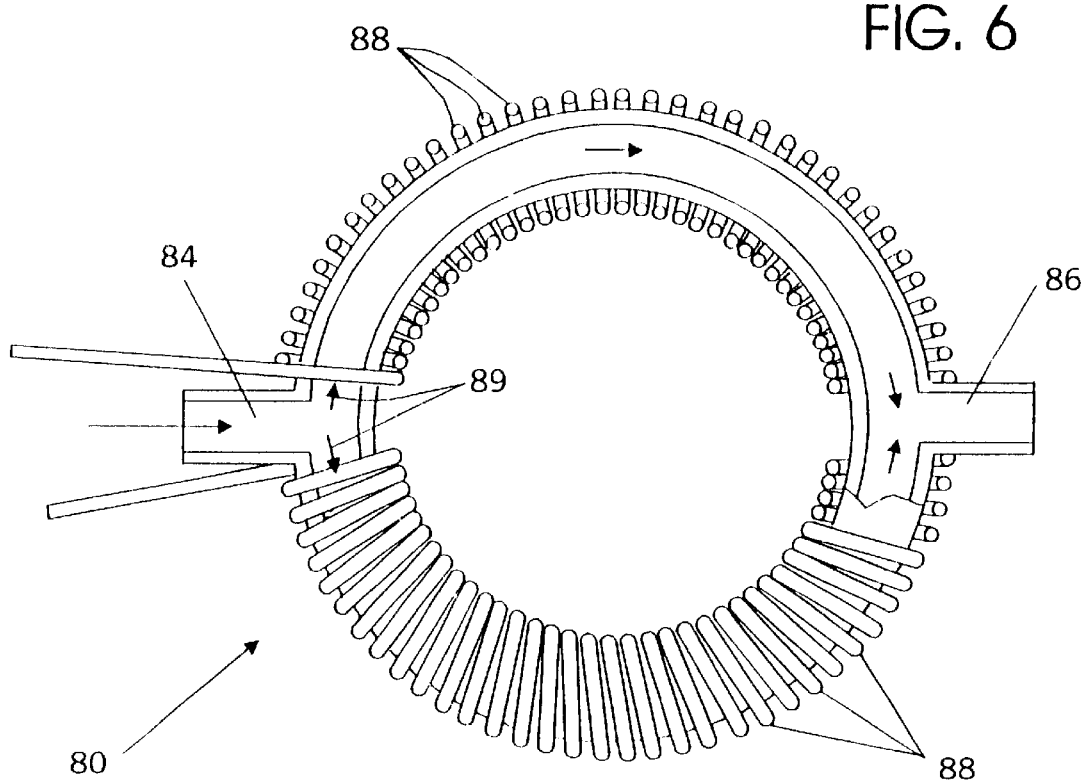
FIG. 6 is an alternate embodiment sensing inductor.
Figure 7:
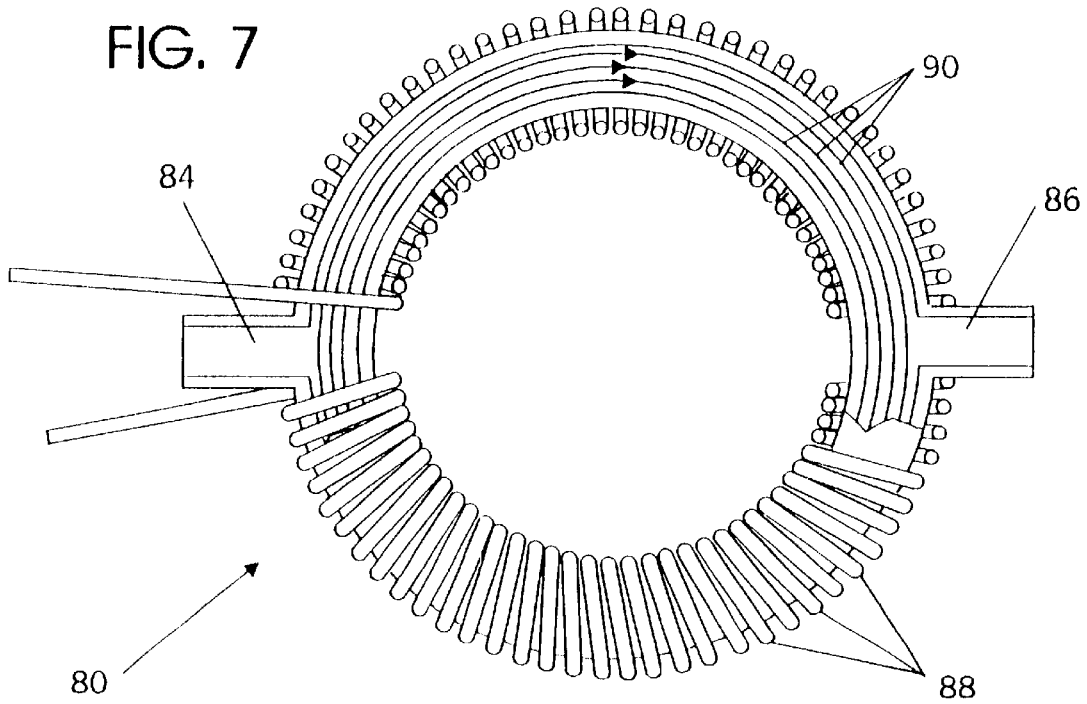
FIG. 7 is the alternate embodiment sensing inductor including the magnetic field produced by the sensing inductor.

An alternate configuration sensing inductor 80 is illustrated in FIG. 6. The sensing inductor 80 provides sensitive measurement of the volume fraction of iron particles in the liquid carrier. The inductor comprises a hollow closed ring 82 with an fluid inlet 84 and a fluid discharge 86. The inductor 80 is flow connected to flow path 11 at the inlet and discharge ends. Magnetic wire 88 is wrapped around the ring. The magnetic wire is the same as previously described hereinabove in sensing inductor 48 of system 10. As shown by arrows 89 in FIG. 6, the fluid flows completely around the ring and as shown in FIG. 7 the magnetic flux 90 is contained substantially entirely inside the coil and as a result, entirely in the magnetically permeable fluid flowing through the ring.

Figure 8:
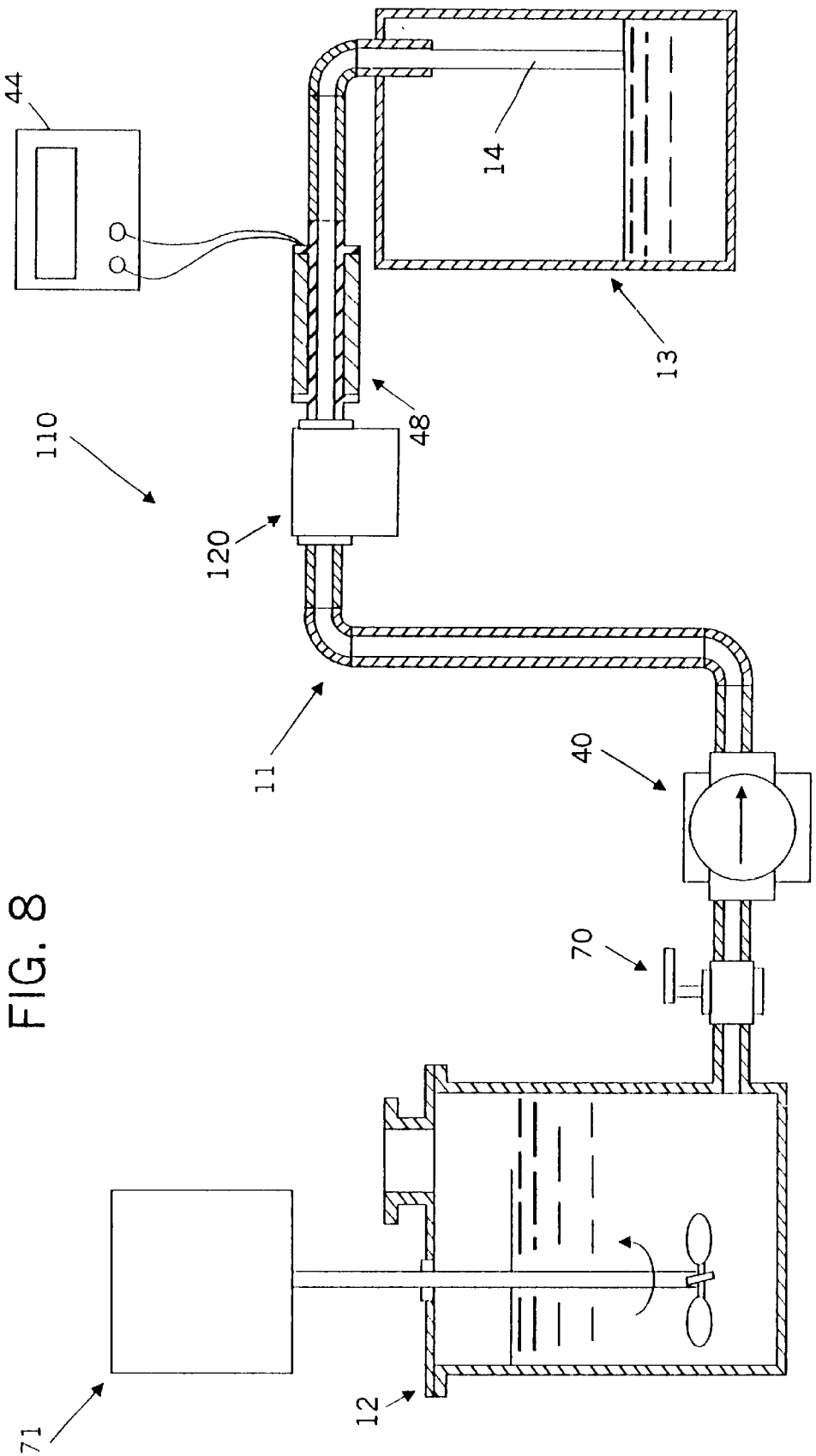
FIG. 8 is a schematic representation of a fourth embodiment of the present invention system for monitoring the composition of a magnetically permeable material.

A fourth embodiment system for monitoring the composition of a magnetically permeable system 110 illustrated in FIG. 8. The system includes containers 12 and 13, flow path 11, valve 70, sensing inductor 48, display device 44, pump 40 and mixing device 71 as previously described hereinabove in systems 10, 100 and 102.

The fourth embodiment system 110 also includes a mass flow sensor 120 flow connected along flow path 11 upstream from the sensing inductor 48. For purposes of describing the preferred embodiment of the invention the mass flow sensor is located upstream from the inductor 48 however, as previously described with the valve, pump and inductor, the mass flow sensor may be located at any suitable position along flow path 11 and does not have to be upstream from the inductor 48. The mass flow sensor 120 may be any suitable device that is able to measure the density of the fluid as it is flowed through flow path 11. More specifically, preferred mass flow sensor is a Coriolis type device well known to one skilled in the art. And more specifically the preferred Coriolis type device is a mass flow sensor sold by Emerson Process Management under the Micro Motion line as model number F-100. The mass flow sensor 120 measures the density of fluid 14 independent of other properties of fluid 14, such as inductance for example. The mass flow sensor may be used independently to determine the particle fraction or may be used in combination with the inductance sensor. The mass flow readings are displayed on the sensor unit. By combining the mass flow readings with the sensed inductance, an operator is able to obtain the accurate particle loading in terms of volume or weight fraction using the inductance and using the fluid density reading is able to determine the type of iron particles in the carrier fluid for example if standard carbonyl oil or reduced carbonyl oil are in the fluid. The measurements provided by the flow sensor and the inductance sensor are combined and as a result, a particle volume fraction is obtained without assuming density or permeability. In this way the system of the present invention provides an accurate, simple and repeatable system and method for maintaining the quality of magnetically permeable fluid. Additionally, from the combined measurement, it is possible to infer the particle density and permeability, thereby providing an independent check or verification that the desired particle has been used to make the fluid.

The mass flow sensor provides an overall density for the magnetically permeable material. The system of the present invention may only include a mass flow sensor to arrive at the particle volume fraction. If the mass flow sensor is used singly to determine the volume fraction of magnetic particles in the material, after obtaining the overall material density from the mass flow sensor the technician or operator assumes a particle permeability in order to infer a volume fraction. In practice, the permeability may be assumed with great accuracy to thereby provide a precise volume fraction value.

Figure 9:
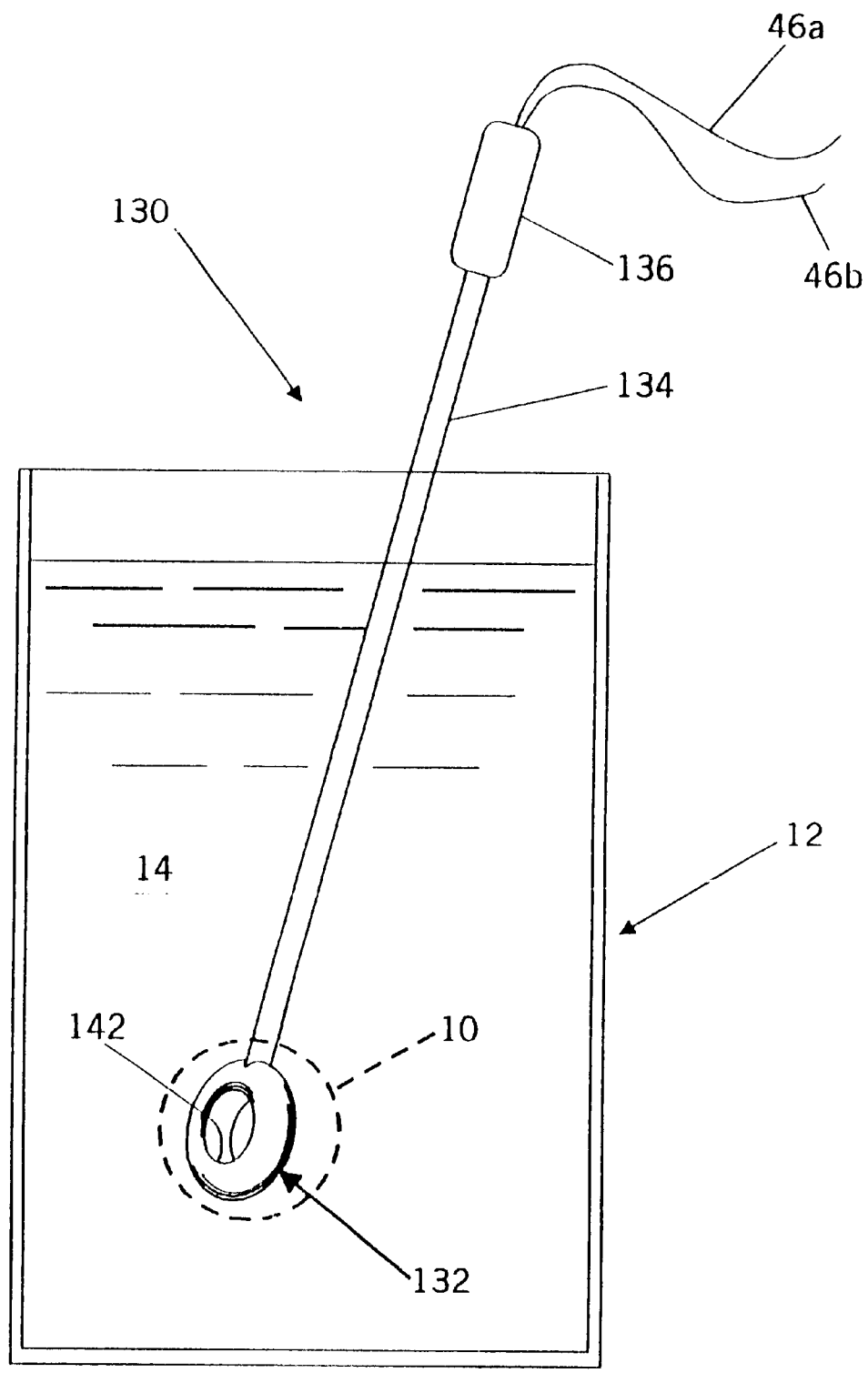
FIG. 9 is an alternate embodiment sensing inductor.
Figure 10:
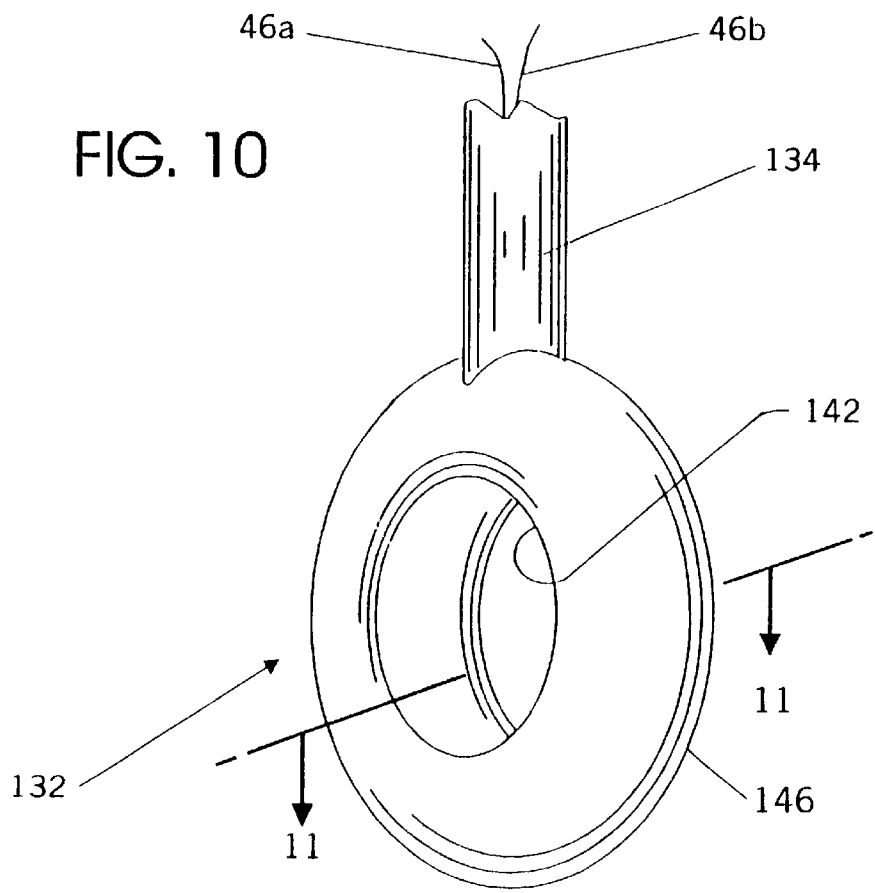
FIG. 10 is an enlarged view of the circled area identified as 10 in FIG. 9.
Figure 11:
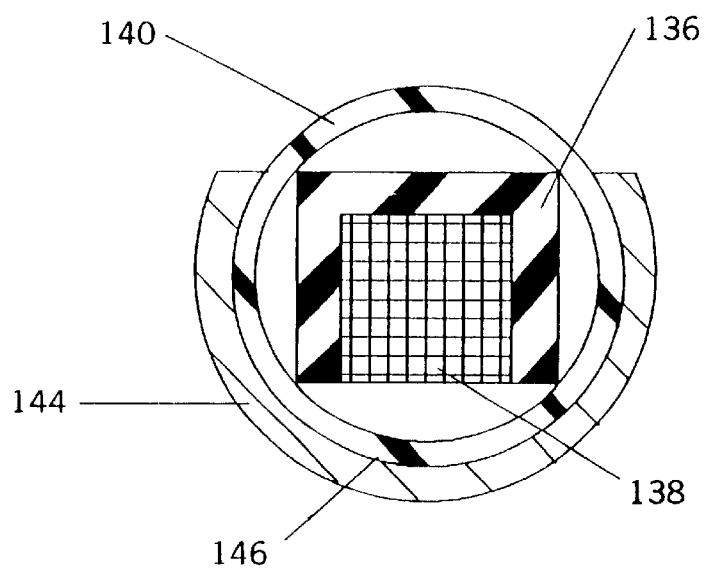
FIG. 11 is a sectional view taken along line 11—11 in FIG. 10.

FIGS. 9–11 illustrate an alternate embodiment sensing inductor 130. The sensing inductor 130 may be combined with the previously described flow path 11, containers 12, 13, valve, 70, mixing device 71, display device 44, and mass sensor 120 in systems 10, 100, 102 and 110. In FIG. 9, the sensing inductor 130 is shown inserted in fluid 14 in container 12 however the probe could also be located in container 13 if required. The inductor 130 is comprised of an inductive coil 132 made integral with shaft or wand 134 at one end of the shaft. A handle 136 is made integral with the opposite end of the shaft connection members 46a and 46b pass through the shaft to electrically connect the ring 132 with display device 44. FIG. 10 is an enlarged view of the ring 132. Inductor 130 may be manually moved around the contained fluid 14 to obtain inductance readings for the fluid. The inductor may be combined with other elements of systems 10, 100, 102 and 110 or may be used solely in combination with container 12 and display 44. When inductor 130 is used, the container 12, 13 should be made from a non-magnetic material. If the container is made from a magnetic material, the ring must be separated from the container walls by a distance.

A detailed sectional view of the hollow ring 132 is illustrated in FIG. 11. As shown in FIG. 11, a non-magnetic annular bobbin 136 supports coil wire 138 which is like previously described coil wire 50 and 88. The bobbin 136 and coil 138 are enclosed by a non-magnetic encapsulant 140 that encloses the bobbin and coil. The magnetic field is again produced by excitation received from display 44 as previously described. The magnetic field acts on magnetically permeable material primarily passing through the opening 142 defined by the ring 132.

The ring may be used without a shield member as shown in FIG. 10, or may include a metal shield 144 along the exterior of encapsulant 140. The shield is located on the outer periphery of the ring 146 and in this way, ensures that the magnetic flux is directed towards the central ring opening 142. The shield is made from any suitable material of high magnetic permeability such as low carbon steel.

The systems of the present invention may be comprised of any suitable combination of elements. For example, the systems may include a sensing inductor and a mass flow meter in combination or they may comprise a sensing inductor or a mass flow meter singly.

While we have illustrated and described preferred embodiments of our invention, it is understood that this is capable of modification, and we therefore do not wish to be limited to the precise details set forth, but desire to avail ourselves of such changes and alterations as fall within the purview of the following claims.

We claim:

1. A system for monitoring the mixed material composition of a manufactured magnetorheological fluid, the system comprising:

A) a first container containing a volume of a mixed manufactured magnetorheological fluid;

B) a flow path for flowing the magnetorheological fluid out of the container;

C) an inductance sensor for sensing the inductance of the magnetorheological fluid; and D) a mass flow meter for sensing the density of the magnetorheological fluid, said density sensor and said inductance sensor being flow connected to the flow path to monitor the mixed material composition of the magnetorheological fluid.

2. The system as claimed in claim 1 wherein the mass flow meter is a Coriolis type device.

3. The system as claimed in claim 1 wherein the inductance sensor is comprised of a hollow member having a coil around the hollow member.

4. The system as claimed in claim 3 wherein the hollow member is tubular.

5. The system as claimed in claim 3 wherein the hollow member is annular.

6. The system as claimed in claim 3 wherein the hollow member and coil are surrounded by a shield.

7. The system as claimed in claim 3 wherein the hollow member includes annular flanges proximate the member ends, the flanges being separated by a distance, the coil being located between the flange members.

8. The system as claimed in claim 1 wherein the system includes a second container, the flow path having an inlet end and a discharge end, the inlet end being located in a first chamber defined by the first container and the discharge end being located in a second chamber defined by the second container.

9. The system as claimed in claim 1 wherein the container defines a chamber and the flow path includes an inlet end and a discharge end, the inlet end being located in the container chamber at a first position, the discharge end being flow connected to the container away from the inlet end.

10. The system as claimed in claim 1 wherein said inductance sensor comprises a hollow member at the end of a shaft.

11. The system as claimed in claim 10 wherein the hollow member is annular.

12. The system as claimed in claim 10 wherein the hollow member is annular and defines a chamber, the member further comprising a bobbin that supports a coil.

13. The system as claimed in claim 12 wherein the hollow member comprises an outer periphery and a shield member along the outer periphery.

14. The system as claimed in claim 1 wherein the manufactured magnetorheological fluid is manufactured by mixing a plurality of iron-particles with a carrier fluid.

15. A system for monitoring the composition of a magnetorheological fluid, the system comprising:
   A) a first container containing a volume of a magnetorheological fluid;
   B) a flow path for flowing the magnetorheological fluid out of the container and through a mass flow meter;
   C) an inductance sensor for sensing the inductance of the magnetorheological fluid; said inductance sensor being flow connected to the flow path.

16. The system as claimed in claim 15 wherein inductance sensor is comprised of a hollow member having a coil around the hollow member.

17. The system as claimed in claim 16 wherein the hollow member is tubular.

18. The system as claimed in claim 16 wherein the hollow member is annular.

19. The system as claimed in claim 16 wherein the hollow member and coil are surrounded by a shield.

20. The system as claimed in claim 15 wherein said inductance sensor is comprised of a hollow member made integral with a shaft, the hollow member defining a chamber that includes a coil.

21. The system as claimed in claim 20 wherein the coil is supported by a bobbin.

22. A system for monitoring the composition of a magnetorheological fluid, the system comprising:
   A) a first container containing a volume of a magnetorheological fluid;
   B) a flow path for flowing the magnetorheological fluid out of the container; and
   C) a density sensor for sensing the density of the magnetorheological fluid, said density sensor being flow connected to the flow path.

23. The system as claimed in claim 22 wherein the mass flow meter is a Coriolis type device.

24. A method of monitoring a composition of a magnetorheological fluid, said method comprising the steps of: providing a first container containing a volume of a magnetorheological fluid, providing a flow path for flowing the magnetorheological fluid out of the container, providing a sensor for sensing an inductance of the magnetorheological fluid, flowing said magnetorheological fluid through said flow path and sensing the inductance of said flowing magnetorheological fluid to monitor the composition of the magnetorheological fluid.

25. The method as claimed in claim 24 wherein providing said container containing said magnetorheological fluid includes mixing a plurality of iron particles with a carrier fluid.

26. A system for monitoring the composition of a magnetorheological fluid, the system comprising:
   A) a first container containing a volume of magnetorheological fluid;
   B) a flow path for flowing the magnetorheological fluid out of the container; and
   C) a means for sensing the inductance of the magnetorheological fluid, said means being flow connected to the flow path.

* * * * *